United States Patent [19]

Calenoff et al.

[11] Patent Number: 4,499,065
[45] Date of Patent: Feb. 12, 1985

[54] CHYMOPAPAIN ALLERGEN AND METHOD

[75] Inventors: Emanuel Calenoff, Burlingame; Ruth M. Jones, Redwood City; Yuh-Geng Tsay, San Jose; Myron A. Beigler, Los Altos Hills, all of Calif.

[73] Assignee: Axonica, Inc., Mt. View, Calif.

[21] Appl. No.: 489,898

[22] Filed: Apr. 29, 1983

[51] Int. Cl.$^3$ .............. A61K 39/35; A61K 49/00; C12N 9/99; C12N 9/50
[52] U.S. Cl. .............................. 424/9; 424/88; 424/94; 435/184; 435/212; 435/219
[58] Field of Search .............. 435/184, 219, 212; 424/88, 94, 9

[56] References Cited

U.S. PATENT DOCUMENTS 4,374,926  2/1983  Stern ........................... 435/219 X
4,439,423  3/1984  Smith ........................... 424/94

OTHER PUBLICATIONS

White et al., Principles of Biochemistry, Fourth Edition, 1968, p. 239.
Ebata et al., Biochemical and Biophysical Research Communications, vol. 9, No. 2, pp. 173–178 (1962).
Ebata et al., Biochim. Biophys. Acta, vol. 118, pp. 201–203 (1966).

*Primary Examiner*—Lionel M. Shapiro
*Attorney, Agent, or Firm*—William B. Walker

[57] ABSTRACT

A chymopapain derivative having the enzymatic activity reduced by at least 95% while retaining the original allergenic activity of at least 90% is suitable for skin testing to detect allergic hypersensitivity to chymopapain and for treating patients exhibiting allergic hypersensitivity to chymopapain. The enzymatic activity can be blocked by reacting thiol groups of the enzyme with and iodoacetic acid, bromoacetic acid, or a salt, ester or amide derivative thereof, under conditions which block the undesirable enzymatic activity while retaining the desired allergenic activity.

14 Claims, No Drawings

CHYMOPAPAIN ALLERGEN AND METHOD

FIELD OF THE INVENTION

This invention relates to therapeutic agents for the desensitizing treatment of allergic hypersensitivity to chymopapain and to their manufacture and use. In particular, this invention relates to the reduction of the allergic hypersensitivity reaction of chymopapain-sensitive patients in order to prepare them for treatment of herniated discs by chymopapain injection.

BACKGROUND OF THE INVENTION

With the medical approval of the non-surgical treatment of prolapsed intervertebral discs by the injection of the proteolytic enzyme chymopapain, a major risk associated with this procedure has become evident. One percent of patients injected with chymopapain have developed symptoms of anaphylactic hypersensitivity ranging from mild urticaria to circulatory collapse, and several have died as a result of this allergic reaction. Because the method involves the injection of a high concentration of chymopapain into the highly confined volume occupied by the disc, the allergic hypersensitivity reaction is greater than would be experienced by ingestion of chymopapain in food. Allergic hypersensitivity to chymopapain is widespread in the population because of the ingestion of chymopapain in food such as papaya, pinapple, fruit juices, beer and meat which has been treated with meat tenderizers. Toothpaste, cosmetics and digestive aids are also suspected as sources of the allergy. Prior to this invention, adequate means have not been available to reduce chymopapain-specific allergic hypersensitivity.

DESCRIPTION OF THE PRIOR ART

A solid phase radioimmunoassay, similar to RAST, has been developed in an attempt to predict anaphylactic reactions in patients injected with the proteolytic enzyme chymopapain, and the results were reported by A. Kapsalis et al., *Clin. Exp. Immunol.* 33, 150–158(1978). A study of 1263 patients was reported. Out of this number, 12 patients had reacted to chymopapain injection, and the RAST test provided a positive result in 7 (58.3 percent) of the 12. Because of the very serious risk of anaphylactic shock associated with the use of chymopapain, the level of accuracy reported was far below that required for practical use.

In our co-pending, commonly assigned application Ser. No. 489,897 filed Apr. 29, 1983 entitled "Fluorometric Assay of Chymopapain and Reagents Therefor" (AX-25), which is filed concurrently herewith and is hereby incorporated by reference in its entirety, an accurate method for detecting and measuring allergic hypersensitivity to chymopapain is described.

A wide variety of allergenic extracts and methods for preparing, storing, and using them for skin tests and desensitization treatment including standard commercial procedures are described in *Remington's Pharmaceutical Sciences*, pp 1344–1352 and 1461–1487, Mack: Easton, Pa., 15th ed. (1975). Allergenic extracts from a wide variety of natural sources are described. Manufacturing procedures for preparing extracts including details about grinding, defatting, extraction, clarification, dialysis, concentration, sterilazation and lyophilization are presented therein.

Major efforts to concentrate and standardize allergenic components of allergen extracts have been made in the past. Procedures for solvent extraction, often combined with precipitation, are described in U.S. Pat. Nos. 2,316,311, 3,148,122, 3,281,323, 3,591,677, 3,953,588, 3,995,023, 4,027,006, and 2,347,435. Ion exchange techniques and procedures for separating components from impurities are described in U.S. Pat. Nos. 4,226,853, 4,234,569, 4,256,732 and 4,163,778. The treatment of allergenic extracts to enhance their stability or to decrease their allergenicity while maintaining their value for desensitization has been proposed in numerous patents and articles. In general, the allergenic proteins are cross-linked with formaldehyde or a similar reagent.

Chymopapain, being a highly active proteolytic enzyme, presents unusual problems not characteristic of previously investigated allergens. Skin tests and desensitization treatments involve the administration of the allergen to a patient. For treating allergic hypersensitivity, desensitizing amounts of allergen are administered for sufficient time and in a carefully designed dosage regimen until the hypersensitivity reaction is reduced or eliminated. Chymopapain, having proteolytic activity, degrades proteins in which it comes in contact. This enzymatic activity causes reactions masking the appearance of allergic reaction flare in the skin tests. The prior art treatments for modification of allergenic activity has been generally directed toward reducing the allergenic activity. Reducing the allergenicity of chymopapain treatment with formaldehyde or other similar reagents renders the product relatively ineffective for desensitization.

Agents effective for blocking enzymatic activity of chymopapain have been described by M. Ebata et al., *Biochem. Biophys. Res. Comm.* 9,173(1962); M. Ebata et al., *Biochem. Biophys. Acta.* 118,210(1966); and A. White et al., *Principles of Biochemistry*, McGraw Hill; New York, p. 240 (1973) which are hereby included in their entirety. Blocking agents described yielded both toxic and non-toxic products and criteria for reducing enzymatic activity while retaining allergenicity are not disclosed. Blocking agents disclosed included heavy metals including cations of silver, mercury, lead; iodoacetates; organomercury compounds such as p-mercuribenzoate; organoarsenic compounds (arsenicals); N-ethylmaleimide and diisopropylphosphofluoridate (DFP).

SUMMARY OF THE INVENTION

The chymopapain derivative of this invention which is suitable for use in skin tests and for desensitizing patients exhibiting chymopapain hypersensitivity has less than 5 percent of the untreated enzymatic activity while retaining at least 90 percent of the allergenic activity of the untreated chymopapain. In one embodiment of this invention, the chymopapain derivative has been chemically modified by converting at least a proportion of the thiol groups thereof to a carboxymethylthio group, a salt thereof, a carbamoylmethylthio (acetamide) group, or a (lower alkoxy)carboxythio group to reduce the enzymatic activity thereof to less than 5 percent of the original enzymatic activity of chymopapain while retaining at least 90 percent of the original allergenic activity of chymopapain.

The chymopapain derivatives of this invention can be prepared by reacting chymopapain in aqueous solution at a temperature within the range of from 4° to 40° C. with a blocking reagent selected from the group consisting of iodoacetic acid, a salt thereof having a non-toxic, pharmaceutically acceptable cation, a lower alkyl ester thereof or iodoacetamide. In this reaction the molar ratio of the blocking reagent to chymopapain is preferably within the range of 100 to 1, and the reaction is carried out until the enzymatic activity of the chymopapain is reduced by 95 percent but before the allergenic activity is reduced to less than 90 percent of that exhibited by the original chymopapain.

The method of this invention for reducing allergic hypersensitivity to chymopapain comprises administering a desensitizing amount of a chymopapain derivative described above.

DETAILED DESCRIPTION OF THE INVENTION

Chymopapain is commercially available as a crystalline solid from which therapeutic solutions are reconstituted for injection into herniated discs. This product is available from Smith Laboratories, Inc. 5433 Milton Parkway, Rosemont, Ill. 60118. Chymopapain is believed to be a composite of at least two separate protein components, and the commercial form is a mixture with non-enzymatic impurities derived from the natural source. This chymopapain is derived from the papaya fruit. Because impurities associated with chymopapain may be allergens and may also present a risk of inducing an allergic hypersensitivity reaction when injected into a patient's disc, it is critical that any desensitization reduce or eliminate hypersensitivity to both the chymopapain and the allergic impurities associated therewith.

To be useful in skin tests for chymopapain allergy and to be safely injected into a patient in desensitization therapy, the proteolytic activity of the chymopapain must be substantially or completely eliminated. The reduction or elimination of the enzymatic activity also must not introduce a pharmaceutically unacceptable or toxic material which would render the product unsuitable for therapeutic treatment. Furthermore, if in the process reducing enzymatic activity, the spectrum of allergens in the chymopapain is significantly altered either by elimination or reduction of an allergenic activity or changing the relative proportions of active allergens, the utility of the product for skin testing and for inducing desensitization of the allergic condition is reduced. In order to completely eliminate a risk of an allergenic hypersensitive reaction, it is critical that desensitization be effected with regard to all components of allergic reaction, and a desensitization agent which eliminates allergic hypersensitivity to only one of several components present in the chymopapain would not eliminate the patient risk.

In general, chymopapain is treated with a blocking reagent which is effective to essentially eliminate enzymatic activity without significantly reducing the allergenic activity of any allergenic component or the relative levels of allergenicity of the various allergens present. A variety of blocking agents effective for eliminating or reducing enzymatic activity of chymopapain have been described by M. Ebata et al., Biochem. Biophys. Res. Comm., supra, p. 173; E. Ebata et al. Biochem. Biophys. Acta., supra, p. 201 and A. White et al., Principles of Biochemistry, supra, p. 240. Blocking agents which introduce toxicity into the final product such as heavy metal cations, heavy metal organometal compounds such as mercurials and arsenicals, and diisopropylphosphofluoridate, while suitable for preparing diagnostic reagents, are not preferred for preparing therapeutic agents because the product is injected during use.

This invention is based upon the discovery that under specific critical conditions, a blocking group derived from iodoacetic or bromoacetic acid, salts thereof having non-toxic pharmaceutically acceptable cations, esters or amides thereof can be highly effective. The method of this invention for modifying the chymopapain to make it suitable for use in skin testing and desensitization comprises reacting the chymopapain in a solution with critical blocking agents under critical conditions.

Suitable blocking agents include bromoacetic acid; iodoacetic acid; and water-soluble salts thereof having non-toxic cations such as alkali metal salts including sodium and potassium salts, alkali earth metal salts including calcium and magnesium salts, ammonium salts, lower alkylamine salts and the like. Bromoacetic and iodoacetic acid esters are also included. The preferred esters include the lower alkyl (from 1 to 6 carbons) esters derived from lower alkanols including methyl, ethyl, n-propyl, isopropyl, n-butyl, isobutyl, t-butyl, pentyl and hexyl alcohols. The corresponding bromoacetamide and iodoacetamide can also be employed. The preferred bromoacetic acid and iodoacetic acid esters include the ethyl esters. Iodoacetic acids, salts, esters and amides are preferred. The term "haloacetic acid compound", as used herein, includes and is hereinafter used to indicate the above-described iodoacetic acid, bromoacetic acid, and their salts, esters and amides.

This reaction is carried out in aqueous solution, the preferred solution being a phosphate buffered saline solution. The haloacetic acid compound and chymopapain are present in a haloacetic acid compound to chymopapain molar ratio of from 10 to 200 and preferably within the range of from 20 to 100. The reagent concentration in the reaction mixture is similarly critical, the chymopapain concentration being within the range of from 0.1 to 50 mg per ml and preferably within the range of from 0.5 to 5 mg per ml. The iodoacetic acid (compound) concentration in the reaction mixture is within the range of from 5 to 90 micrograms per ml and is preferably within the range of from 10 to 50 micrograms per ml.

For an optimum reaction, a number of other parameters are important in the reaction mixture. The pH should be within the range of from 4 to 9 and is preferably from within the range of 6 to 8. The reaction is advantageously carried out at a temperature of from 4° to 40° C. and is preferably carried out at a temperature of from 4° to 22° C. The reaction time is dependent upon the reaction temperature, the higher temperatures requiring shorter reaction times. For reactions within the range of from 4° to 22° C., reaction times of from one to 16 hours are preferred. The ultimate criterion however, is the desired degree of reduction of enzymatic activity with retention of allergenic activity.

Following the reaction, purification of the chymopapain derivative is achieved by conventional purification procedures such as dialysis, gel filtration, chromatography, ultrafiltration and ion exchange chromatography.

Following purification, the chymopapain derivative is dried to a moisture content of less than 2 weight percent, preferably by lyophilization or similar freeze-drying techniques, and sealed. The product can be stored for up to 5 years at temperatures of within the range of from $-20°$ to 8° C.

Key to special treatment of chymopapain allergic hypersensitivity is the accurate titration of the patient to determine the desensitization dosage. A variety of techniques are available to carry out this procedure. Examples of traditional procedures are described in *Remington's Pharmaceutical Sciences,* supra, pp 1344–1352, the entire contents of which are incorporated herein by reference.

The cutaneous or scratch test is performed according to this invention by scarifying or making small abrasions on the skin of the patient and applying a small amount of reconstituted enzymatically inactive chymopapain of this invention. A positive reaction is indicated by a hive-like swelling and redness at the point of application, and is known clinically as a "wheal or flare" reaction. The reaction occurs in allergic individuals usually within 15 to 20 minutes. The size and appearance of the reaction provides a measure of the degree of sensitivity. Intracutaneous or intradermal testing is accomplished by injecting the reconstituted enzymatically inactive chymopapain between layers of skin and observing the reaction. This test is more sensitive than the scratch test. Patch testing is a diagnostic procedure in which a small square of gauze or blotting paper, impregnated with reconstituted enzymatically inactive chymopapain, is applied directly to the skin in order to elicit symptoms of allergic contact dermatitis. A reading is taken after 48 hours. The enzymatically inactive chymopapain can be applied in a serial fashion, that is, can be applied in graduated and increased doses so as to identify the concentration-sensitivity relationship.

A highly sensitive procedure for carrying out this test is described in our commonly assigned, co-pending application entitled Fluorometric Assay of Chymopapain and Reagents Therefor, application Ser. No. 489,897 concurrently herewith, the contents thereof being hereby incorporated by reference. In general, the fluorometric assay described in that application comprises a first step of contacting an insoluble support having an allergenically active chymopapain adhered thereto with patient's serum for a sufficient time to permit binding of the chymopapain on the insoluble support with chymopapain-specific IgE antibody present in the serum. After binding, the serum is removed from the insoluble support, and the support is contacted with a solution of labeled anti-IgE antibody for sufficient time to permit binding of the anti-IgE antibody with any IgE antibody bound to the insoluble support. This solution is removed, and the amount of anti-IgE antibody bound to the insoluble support or in the solution removed therefrom is measured. Preferably, the labeled anti-IgE antibody is conjugated with a fluorogenic enzyme, and the amount of enzyme-labeled IgE antibody bound to the insoluble support is measured by contacting the insoluble support with a substrate which, in the presence of the fluorogenic enzyme, releases fluorescent compound. The amount of fluorescence in the solution is then measured. Optimally, the anti-IgE antibody is a monoclonal antibody.

In the method of desensitization therapy, the chymopapain derivative is reconstituted and injected in sufficient quantity to cause major production of chymopapain-specific IgG and major production and/or activation of suppressor T-Lymphocytes. However, the quantity should not be sufficient to cause major allergic reaction and excessive chymopapain-specific IgE production. To the extent that chymopapain-specific IgE is produced at an increased level, it is critical that the IgG and suppressor IgE production is in such balances to prevent further allergic reaction.

The concentration and amount of the desensitization dosage are dependent upon many factors which are specific to the subject having the chymopapain hypersensitivity. It is therefore necessary to titrate the patient to determine the proper dosage. A variety of standard techniques are available to carry out this procedure. In general, once the desensitization range is identified, for example, from the fluorometric assay described above, increasing doses of chymopapain derivative are administered, the amounts being increased over a period of time until the desired desensitization is achieved.

The chymopapain derivative can be administered in the above methods by subcutaneous, intradermal, or intramuscular injection or it can be administered orally, by inhalation, rectally or by other accepted means. The chymopapain derivative concentration is administered in a quantity of from 0.1 to 10,000 micrograms of antigen per injection.

The desensitization procedure involves injecting into the patient gradually increased doses of the composition of this invention, usually to maximum tolerated doses (doses not giving rise to major allergic response), at varying intervals in an attempt to develop IgG antibody protection against chymopapain, and to increase the specific suppressor T-Lymphocyte activity responding to chymopapain hypersensitivity. The exact mechanisms of this process are not fully understood. Booster injections to maintain the requisite IgG and suppressor T-Lymphocyte levels are required at intervals of from one to four weeks. Usually the doses required for booster injections are substantially greater than the maximum dose required for control of the initial allergic reaction.

Once the desired desensitization is achieved, chymopapain can be safely used to treat herniated discs.

The injectable composition of this invention is an aqueous composition which contains the chymopapain derivative in combination with one or more pharmaceutically acceptable, non-toxic excipients. For the injectable formulations, the concentration of chymopapain is not critical and is determined by the dose needed per injection. In general, chymopapain concentrations of from 10 to 100,000 micrograms per ml can be used in the injectable composition.

The composition of this invention is used in an aqueous formulation. Certain aqueous vehicles are recognized officially because of their valued use in parenteral formulations. Often they are used as isotonic vehicles to which the chymopapain can be added at the time of administration. The additional osmotic effect of the chymopapain should not be enough to produce any discomfort when administered. These vehicles include Sodium Chloride, Injection, Ringer's Injection, Coca's Solution, Evan's Solution, Dextrose Injection, Dextrose and Sodium Chloride Injection and Lactated Ringer's Injection. The injectable compositions must be free from microbial and particulate contamination, free from pyrogen contamination, and to the extent they contain suspended solids, should be easily dispersed to form an injection mixture having a uniform concentration.

The excipients added can be those generally used for parenteral compositions. In general these fall into categories of isotonic salts, antimicrobial agents, buffers and antioxidants.

Any water-soluble, non-toxic salts generally used in adjusting the tonicity of parenteral solutions can be used. Sodium chloride is most commonly used. Other suitable salts are listed in *Remington's Pharmaceutical Sciences,* supra, pp 1405–1412 together with their isoosmotic concentration, the contents of which are hereby incorporated by reference. Antimicrobial agents and bacterial static or fungistatic concentrations can be added, particularly in preparations contained in multidose containers. They must be present in adequate concentration at the time of use to prevent the multiplication of microorganisms inadvertently introduced into the preparation while withdrawing a portion of the contents with a hypodermic needle and syringe. The compounds generally approved in the concentration limit prescribed for each is set forth in United States Pharmacopeia (USP). Suitable antimicrobial agents include phenylmercuric nitrate, thimerosal 0.01%, benzethonium chloride and benzalkonium chloride 0.01%, phenol or cresol 0.5%, and chlorobutanol 0.5%. These concentrations are stated as those in the parenteral composition. Phenylmercuric nitrate is frequently employed in a concentration of 0.002%. Methyl p-hydroxybenzoate 0.18% and propyl p-hydroxybenzoate 0.02%, in combination, and benzyl alcohol 2% are also suitable.

The buffers are used primarily to stabilize a solution against the chemical degradation that would occur if the pH changed appreciably. Buffer systems employed should normally have as low a buffer capacity as feasible in order not to disturb significantly the body's buffer systems when injected. In addition, the buffer range and the effect of the buffer on the activity of the antigen is of concern. The acid salts most frequently used as buffers are water-soluble salts such as sodium, potassium, and ammonium citrates, acetates and phosphates.

Protein stabilizers such as water-soluble animal or vegetable proteins can be used to preserve the chymopapain derivative against deterioration during prolonged storage due to oxidation. Suitable water-soluble proteins include serum albumins of bovine (BSA), human (HSA), rabbit (RSA), goat (GSA), sheep (SSA), horse (HOSA), etc.; serum gamma Globulin of the previously described animals; and other animal proteins such as ovalbumin, fribrinogen, thrombin, transferrin, glycoproteins, etc. Suitable water-soluble amino acid polymers include polymethionine, polyproline, etc.

The anhydrous chymopapain derivative of this invention is stable, free from water (less than one percent water) and impurities. It can be free of excipients or it can contain pharmaceutically acceptable, non-toxic excipients which, when reconstituted with water or with normal parenteral solutions yield a composition suitable for parenteral administration according to the method of this invention. The amounts of antimicrobial agents and antioxidants present, if any, should yield a final concentration in a parenteral solution which falls within the range of those concentrations for each agent approved by the USP.

In general, the stable chymopapain derivative contains from 0.01 to 99.9 weight percent of chymopapain derivative. It can also optionally contain from 0 to 2 and preferably from 0.1 to 0.5 weight percent antimicrobial composition, and from 0 to 5 and preferably from 0.1 to 2 weight percent protein stabilizer. If the dry concentrate is to be mixed with a buffered isotonic parenteral solution to form the final parenteral injectable composition, it is unnecessary to have buffers and isotonic salts present in the dry concentrate. However, if the dry concentrate is to be reconstituted with distilled water, then it can contain from 0.1 to 5 and preferably from 0.5 to 2 weight percent buffering compound such as monobasic potassium phosphate, dibasic sodium phosphate, sodium bicarbonate or the like and a sufficient quantity of an isotonic salt such as sodium chloride to provide an isotonic solution.

The parenteral composition for injection can be prepared from a dry concentrate, as indicated above, by mixing the concentrate with standard parenteral solutions, or alternatively, it can be reconstituted with distilled water. Typical standard parenteral solutions include Buffered Saline, Coca's Solution, Glycerinated Coca's Solution, Isotonic Sodium Chloride Solution, Sodium Bicarbonate Solution, Glycerin Saline Solution, Alcohol Saline Solution, Dextrose Solution 5%, and Dextrose Saline Solution. These solutions and their preparation are described in most pharmaceutical handbooks such as *Remington's Pharmaceutical Sciences,* supra, pp 1345, 1461–1487, which are hereby incorporated by reference.

This invention is further illustrated by the following specific but non-limiting examples. Concentrations are given as weight percents and temperatures as degrees Centigrade unless otherwise specified.

EXAMPLE 1

To 1.0 ml of solution comprising 1.0 mg of chymopapain in a phosphate buffer solution (PBS), pH 6.0, is added 10 microliters of 0.0004M iodoacetic acid in the same buffer solution. The mixture is maintained at 4° C. for 16 hr, and then dialyzed against 0.1M phosphate buffer solution at successive pH's of 6, 7 and 8.

The degree of enzymatic activity reduction is determined by applying 10 microliters of the solution of deactivated enzyme to 3 mm wells punched in a casein agar gel (BioRad Protease Detection Kit). Protease activity is determined by the size of the clear area, if any, in the white gel. The enzymatic deactivation can also be confirmed by mixing the deactivated enzyme (and natural chymopapain as a control) to a solution of the substrate, N-alpha-benzoyl-L-Arginine ethyl ester, and measuring the products spectrophotometrically at 253 nm.

EXAMPLE 2

Repeating the procedure of Example 1 but replacing the iodoacetic acid with iodoacetic acid, sodium salt; iodoacetic acid, postassium salt; iodoacetic acid, ammonium salt; bromoacetic acid; bromoacetic acid, sodium salt; bromoacetic acid, potassium salt; bromoacetic acid, ammonium salt; ethyl iodacetate; propyl iodoacetate; ethyl bromoacetate; propyl bromoacetate; iodoacetamide and bromoacetamide yields, in each instance, enzymatically deactivated chymopapain.

EXAMPLE 3

The product of Example 1 is lyophilized by being placed in vials, each vial containing the equivalent of 100,000 Allergy Units (FDA recommended standard). The vials are frozen to −30° C. for 2 hours, vacuum is applied, the lyophilizer shelf is gradually heated to 25° C., and the freeze-drying is continued until constant weight is achieved to yield vials containing 100,000 units of deactivated chymopapain having a moisture content of less than one wt.%.

EXAMPLE 4

The lyophilized enzymatically inactive chymopapain product of Example 3 is reconstituted with 5 ml Delveccio's PBS solution having the following composition.

| | |
|---|---|
| Potassium Chloride | 0.20 g/l |
| Potassium dihydrogen phosphate | 0.20 g/l |
| Sodium Chloride | 8.00 g/l |
| disodium phosphate ($Na_2HPO_4.7H_2O$) | 2.16 g/l |
| Distilled water | qs 1.00 l |

The invention claimed is:

1. A chymopapain derivative, the enzymatic activity thereof being less than 5% of the enzymatic activity of natural chymopapain, and the allergenic activity being at least 90% of the allergenic activity of the natural chymopapain.

2. A chymopapain derivative of claim 1, sufficient thiol groups thereof having been converted to a carboxymethylthio group or a salt thereof, a carbamoylmethylthio group, or a (lower alkoxy)carbonylthio group to reduce the enzymatic activity thereof to less than 5 of the enzymatic activity of natural chymopapain while retaining at least 90% of the allergenic activity of natural chymopapain.

3. A chymopapain derivative of claim 1 wherein the thiol group thereof has been converted to a carboxymethylthio group or a salt thereof, the cation thereof being pharmaceutically acceptable.

4. A chymopapain derivative of claim 1 wherein from at least 95% of the thiol groups have been converted to carboxymethylthio groups or a salt thereof.

5. A method for reducing enzymatic activity of chymopapain comprising reacting chymopapain in an aqueous solution having a pH of from 4 to 9 at a temperature within the range of from 4° to 40° C. with a haloacetic acid compound selected from the group consisting of iodoacetic acid, a salt thereof, a lower alkyl ester thereof; bromoacetic acid, a salt thereof, a lower alkyl ester thereof; bromoacetamide; and iodoacetamide, the molar ratio of the haloactic acid compound to chymopapain being within the range of from 10 to 200, until the enzymatic activity of the chymopapain is reduced by 95% but before the allergenic activity of the chymopapain is reduced to less than 90%.

6. The method of claim 5 wherein the haloacetic acid compound is iodoacetic acid or a salt thereof having a pharmaceutically acceptable cation, and the reaction is carried out in an aqueous solution containing from 0.1 to 50 mg per ml of chymopapain and from 5 to 90 micrograms per liter of iodoacetic acid or a salt thereof.

7. The method of claim 6 wherein the aqueous solution has a pH of from 6 to 8, and the reaction is carried out at a temperature of from 4° to 22° C.

8. The product produced by the method of claim 5.

9. The product produced by the method of claim 6.

10. The product produced by the method of claim 7.

11. A method for treating a patient having hypersensitivity to chymopapain comprising administering a desensitizing amount of a pharmaceutically acceptable chymopapain derivative of claim 1 to the patient.

12. A method for treating a patient having hypersensitivity to chymopapain comprising administering a desensitizing amount of a pharmaceutically acceptable product of claim 5 to the patient.

13. A method for detecting chymopapain allergic hypersensitivity comprising carrying out a skin test with a pharmaceutically acceptable chymopapain derivative of claim 1.

14. A method for detecting chymopapain allergic hypersensitivity comprising carrying out a skin test with a product of claim 5.

* * * * *